United States Patent [19]

Dennehey et al.

[11] 4,439,188
[45] * Mar. 27, 1984

[54] TUBE CONNECTOR

[75] Inventors: T. Michael Dennehey, Arlington Heights; Richard J. Greff, Ingleside; Ludwig Wolf, Jr., Crystal Lake, all of Ill.

[73] Assignee: Baxter Travenol Laboratories, Inc., Deerfield, Ill.

[*] Notice: The portion of the term of this patent subsequent to Aug. 31, 1999 has been disclaimed.

[21] Appl. No.: 378,029

[22] Filed: May 13, 1982

Related U.S. Application Data

[63] Continuation of Ser. No. 187,008, Sep. 15, 1980, Pat. No. 4,346,703, which is a continuation-in-part of Ser. No. 27,419, Apr. 5, 1979, abandoned, which is a continuation-in-part of Ser. No. 5,748, Jan. 23, 1979, abandoned.

[51] Int. Cl.³ .............................................. A61M 5/00
[52] U.S. Cl. ....................................... 604/283; 604/29
[58] Field of Search ................. 604/29, 240, 241, 242, 604/243, 283; 285/12, 332, 423, 174, 242

[56] References Cited

U.S. PATENT DOCUMENTS

| Re. 28,334 | 2/1975 | Cranage . |
|---|---|---|
| 962,027 | 6/1910 | Kennedy . |
| 1,137,551 | 4/1915 | Taby et al. . |
| 1,150,420 | 8/1915 | Davis et al. . |
| 1,289,714 | 12/1918 | Elkin . |
| 1,846,877 | 2/1932 | Knapp . |
| 2,247,843 | 7/1941 | Kamenarovic . |
| 2,757,672 | 8/1956 | Ogle ..................................... 604/241 |
| 2,858,848 | 11/1958 | Wittren . |
| 2,886,623 | 5/1959 | Lehr . |
| 3,109,383 | 11/1963 | Muller . |
| 3,127,892 | 4/1964 | Bellamy et al. . |
| 3,211,150 | 10/1965 | Foderick . |
| 3,344,786 | 10/1967 | Berg et al. . |
| 3,399,677 | 9/1968 | Gould et al. . |
| 3,426,759 | 2/1969 | Smith . |
| 3,478,743 | 11/1969 | Ericson . |
| 3,482,572 | 12/1969 | Grosclaude et al. . |
| 3,484,121 | 12/1969 | Quinton . |
| 3,502,355 | 3/1970 | Demler et al. . |
| 3,508,546 | 4/1970 | Rogers et al. . |
| 3,514,131 | 5/1970 | McKinney . |
| 3,538,950 | 11/1970 | Porteners . |
| 3,731,691 | 5/1973 | Chen . |
| 3,976,311 | 8/1976 | Spendlove . |
| 4,000,739 | 1/1977 | Stevens . |
| 4,008,717 | 2/1977 | Kowarski . |
| 4,022,205 | 5/1977 | Tenczar . |
| 4,031,891 | 6/1977 | Jess . |
| 4,076,285 | 2/1978 | Martinez . |
| 4,080,965 | 3/1978 | Phillips . |
| 4,094,536 | 6/1978 | Cole et al. . |
| 4,123,091 | 10/1978 | Cosentino et al. . |
| 4,133,312 | 1/1979 | Burd . |
| 4,137,930 | 2/1979 | Scholle . |
| 4,161,949 | 7/1979 | Thanawalla . |
| 4,187,846 | 2/1980 | Lolachi et al. . |
| 4,187,848 | 2/1980 | Taylor . |
| 4,195,632 | 4/1980 | Parker et al. . |
| 4,201,208 | 5/1980 | Cambio, Jr. . |
| 4,239,041 | 12/1980 | Popovich et al. . |

FOREIGN PATENT DOCUMENTS

| 481323 | 2/1950 | Australia . |
|---|---|---|
| 484504 | 2/1951 | Australia . |
| 994631 | 10/1976 | Canada . |
| 15993 | 2/1881 | Fed. Rep. of Germany . |
| 2124793 | 12/1971 | Fed. Rep. of Germany . |
| 2853635 | 6/1972 | Fed. Rep. of Germany . |
| 2312478 | 9/1973 | Fed. Rep. of Germany . |
| 2331687 | 10/1973 | Fed. Rep. of Germany . |
| 7829185 | 11/1980 | Fed. Rep. of Germany . |
| 7107512 | 6/1983 | Fed. Rep. of Germany . |
| 1528025 | 3/1948 | France . |
| 1434709 | 2/1963 | France . |
| 2395037 | 1/1965 | France . |
| 33-2595 | 2/1968 | Japan . |
| 53-49897 | 4/1972 | Japan . |
| 52-27277 | 2/1973 | Japan . |
| 48-54799 | 5/1973 | Japan . |
| 50-23551 | 3/1980 | Japan . |
| 402286 | 8/1980 | Switzerland . |
| 2000685 | 3/1953 | United Kingdom . |
| 1046684 | 5/1960 | United Kingdom . |
| 2024974 | 4/1963 | United Kingdom . |

OTHER PUBLICATIONS

Odel et al., "Peritoneal Lavage as an Effective Means of

Extra Renal Excretion", American Journal of Medicine, vol. 9, 7–1950, pp. 63–77.
Grollman et al., "Intermittent Peritoneal Lavage in Nephrectomized Dogs and Its Application to the Human Being", *AMA Archives in Internal Medicine*, 1951, pp. 379–390.
Waugh, "Successful Use of Simplified Method of Intermittent Peritoneal Dialysis", *Journal of Urology*, vol. 72, Dec. 1954, pp. 1094–1103.
"Dimensions of Glass and Metal Luer Tapers for Medical Applications", *USA Standard*, USAS Z 70-1-1955.
German Publication DIN 13090.

*Primary Examiner*—C. Fred Rosenbaum
*Assistant Examiner*—T. J. Wallen
*Attorney, Agent, or Firm*—Paul C. Flattery; George H. Gerstman; Garrettson Ellis

[57] ABSTRACT

Equipment for continuous ambulatory peritoneal dialysis in which a solution container is coupled via flexible tubing to a patient's tube that communicates with the patient's peritoneal cavity by means of a catheter, usually a surgically implanted catheter. The equipment includes a flexible, foldable plastic dialysis solution container having a transfer port. A flexible tube having a luer connector at its distal end extends from the transfer port, for connecting to a luer connector carried by the patient's tube. The flexible tube carries a frangible member which normally blocks fluid flow but permits fluid flow after the frangible member is broken. A particulate filter and a manually-operable clamp are in series with the flexible tube.

Peritoneal dialysis is accomplished by connecting the luer connector from a fresh dialysis solution bag to the patient's tube luer connector, breaking the frangible member, and opening the clamp on the flexible tubing. After the dialysis solution is introduced into the patient's peritoneal cavity and remains there for a predetermined time, the solution is drained back into the flexible bag, the luer connectors are disconnected and the foregoing steps are repeated. If desired, once the dialysis solution has been introduced into the patient's peritoneal cavity, the luer connections may be disconnected and the patient's tube luer connector may be capped.

12 Claims, 20 Drawing Figures

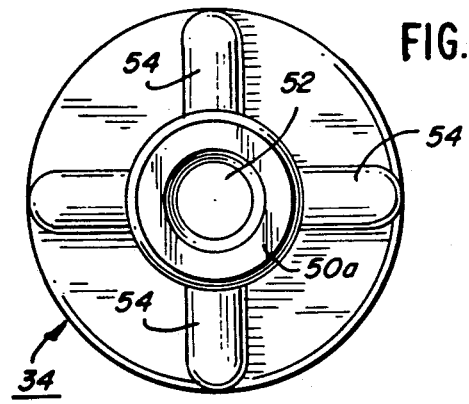
FIG. 2
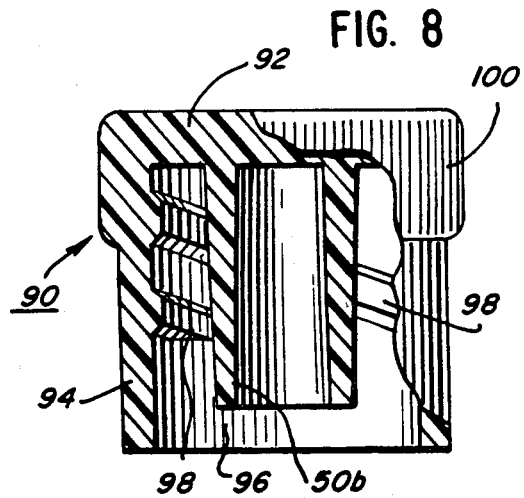
FIG. 8
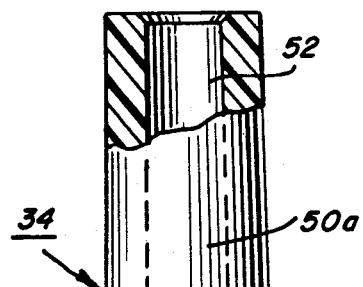
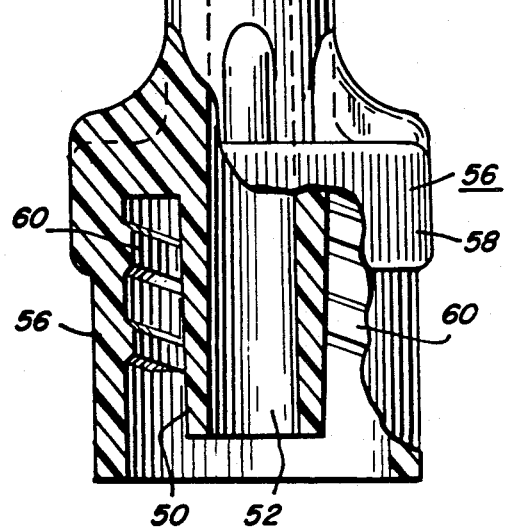
FIG. 3
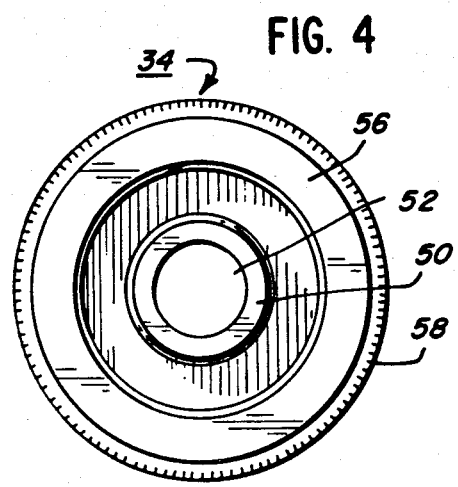
FIG. 4

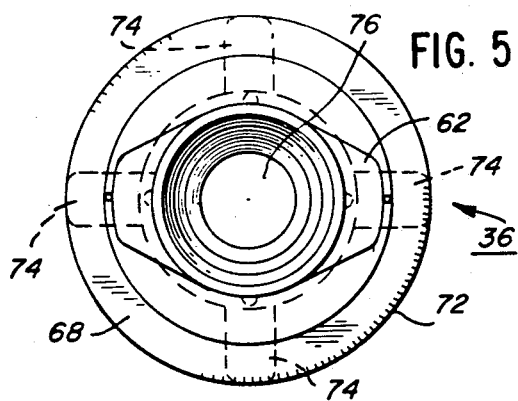
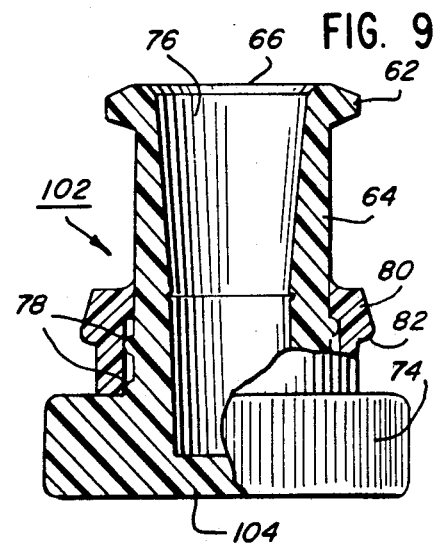
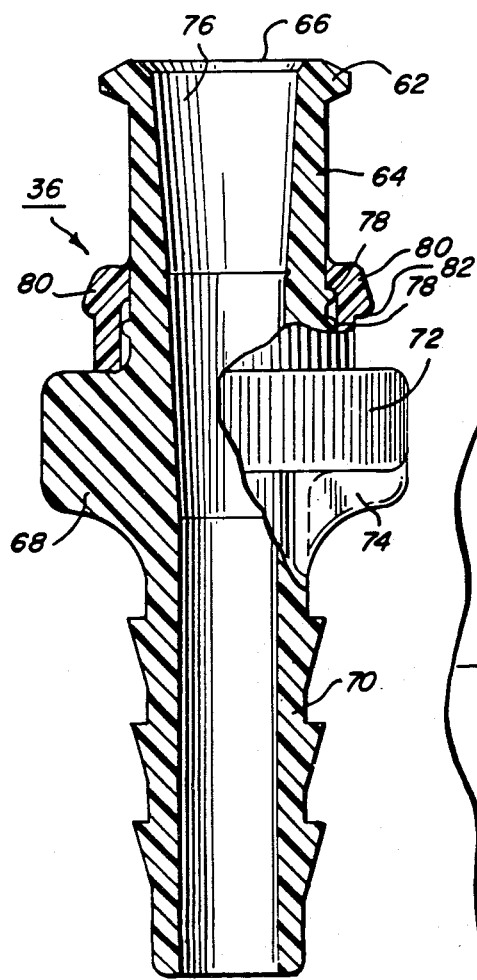
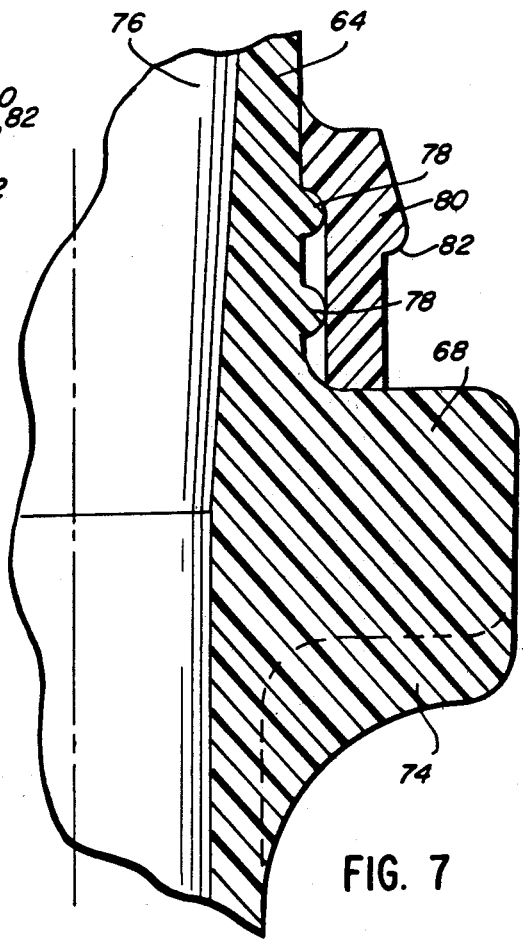

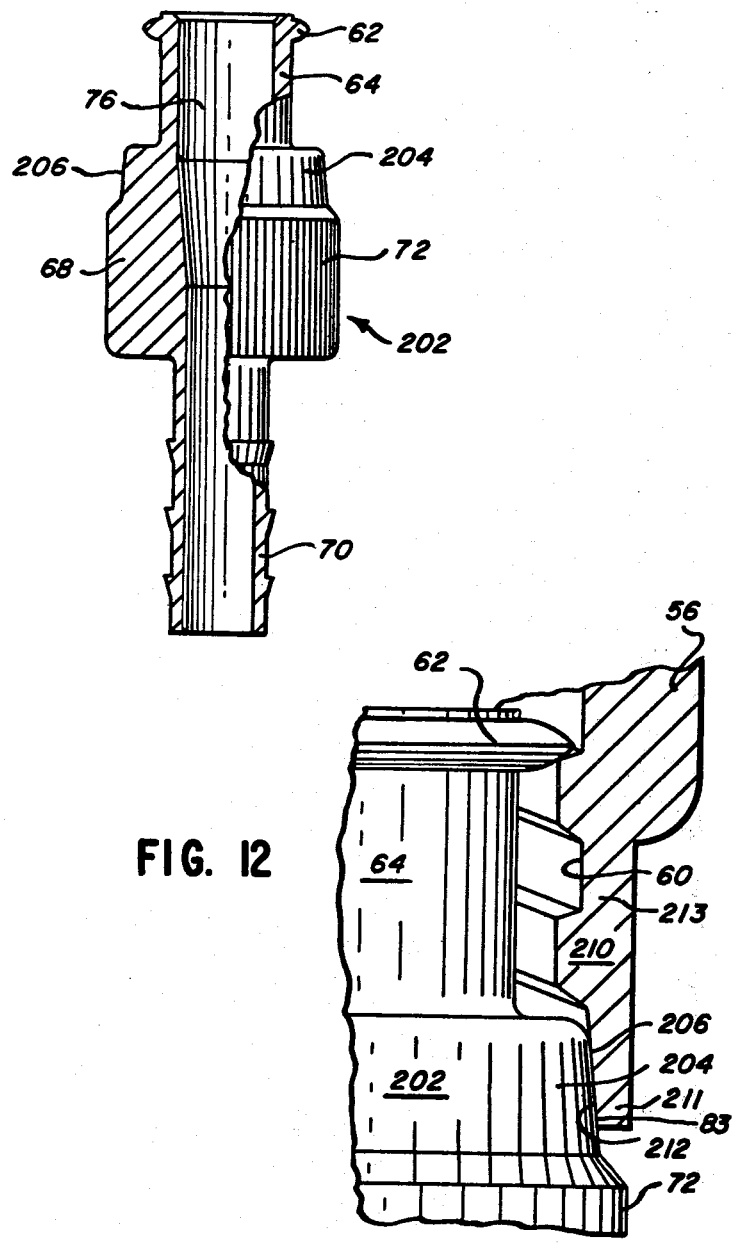

FIG. 14
FIG. 15
FIG. 16
FIG. 17
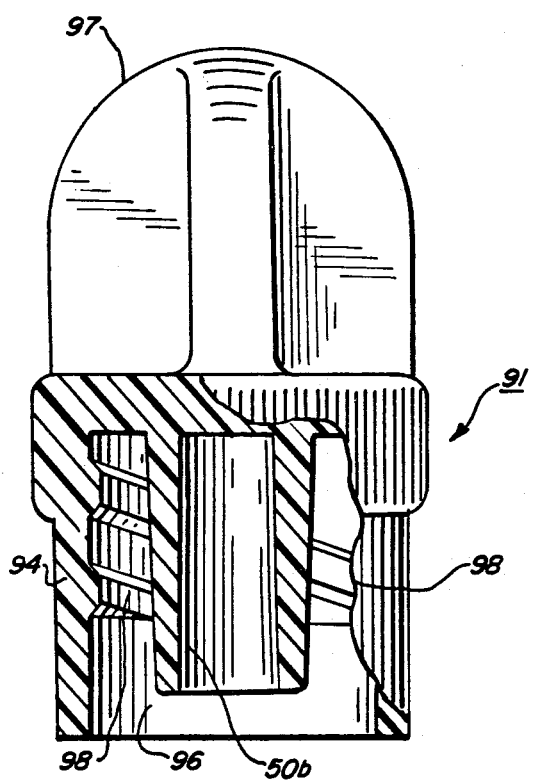
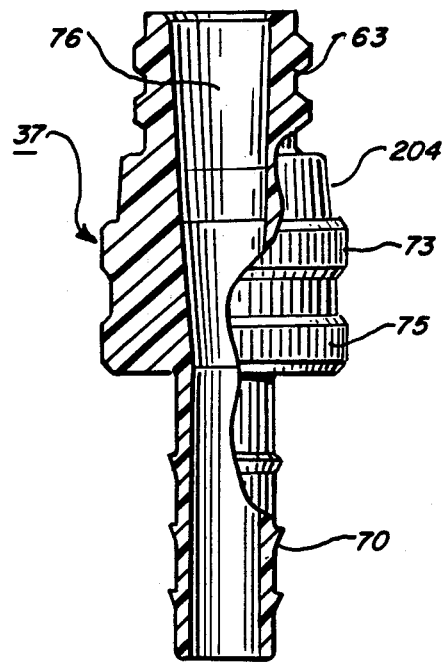
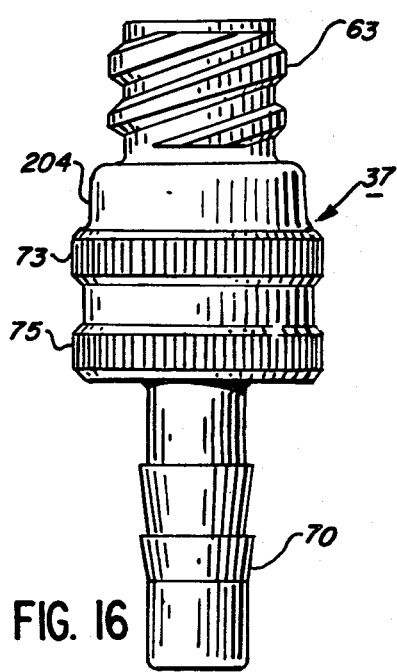
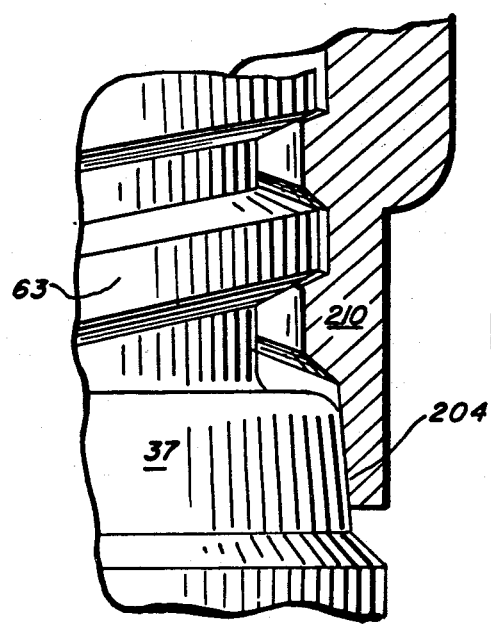

FIG. 18
FIG. 19
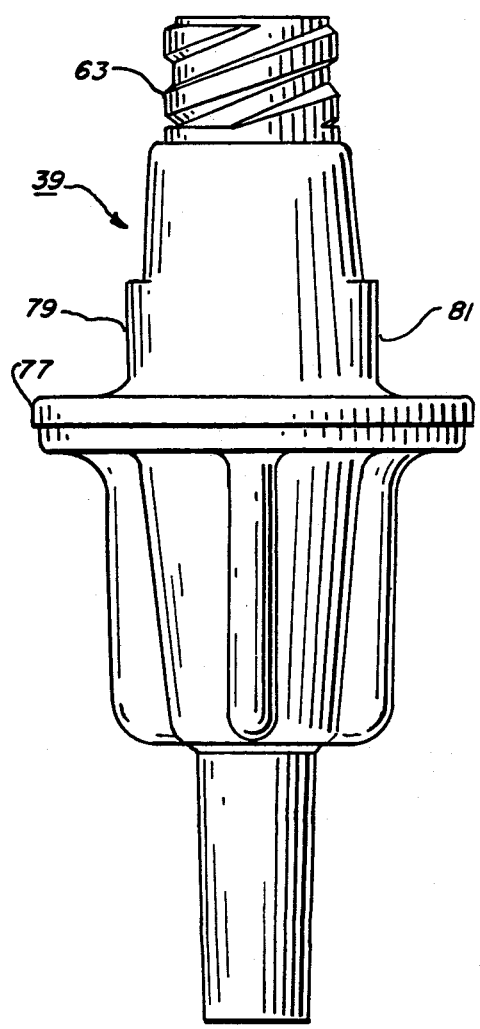
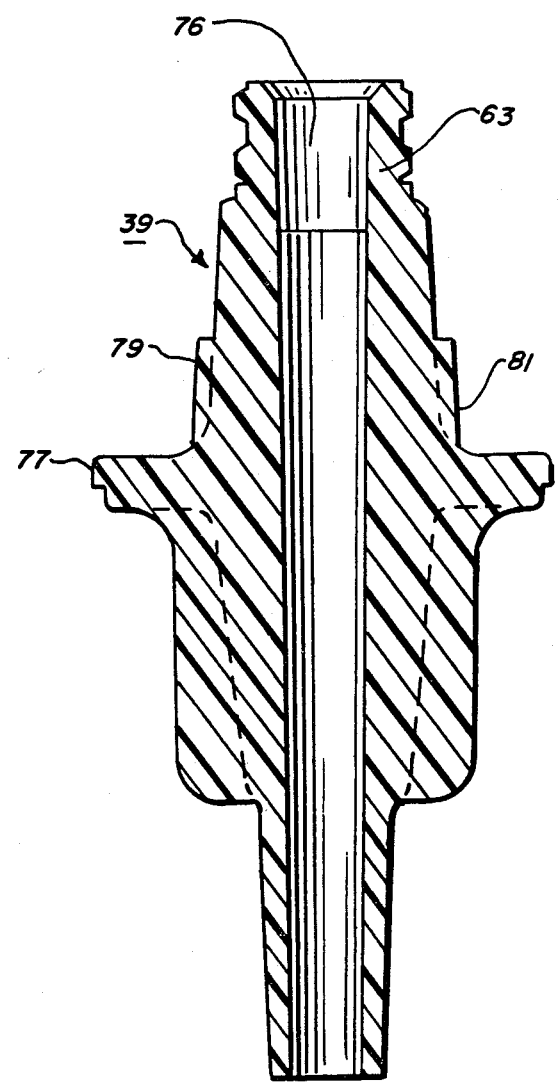

TUBE CONNECTOR

This application is a division of application Ser. No. 187,008, filed Sept. 15, 1980, now U.S. Pat. No. 4,346,703, which in turn is a continuation-in-part of application Ser. No. 27,419, filed Apr. 5, 1979, now abandoned, which is a continuation-in-part of application Ser. No. 5,748, filed Jan. 23, 1979, now abandoned.

BACKGROUND OF THE INVENTION

This invention concerns equipment for continuous ambulatory peritoneal dialysis and, more particularly, a novel solution container for continuous ambulatory peritoneal dialysis and a novel luer lock assembly for use therewith and for use in other medical applications.

The present invention is particularly suited for use in continuous ambulatory peritoneal dialysis in which a dialysis solution is introduced to the peritoneal cavity of the patient, allowed to remain there for several hours and then drained from the patient's peritoneal cavity with this process being repeated on a substantially continuous basis. One manner of achieving this type of dialysis includes the steps of connecting a dialysis solution container to a catheter connected to the patient's peritoneal cavity, unclamping the tubing between the dialysis solution container and the patient's peritoneal cavity so as to allow the dialysis solution to flow from the container to the peritoneal cavity, thereafter reclamping the tubing, allowing the dialysis solution to remain within the patient's peritoneal cavity for several hours, for example, four hours, unclamping the tubing and draining the solution from the patient's peritoneal cavity back to the dialysis solution container, disconnecting the dialysis solution container from the catheter tube and connecting to the catheter tube a fresh dialysis solution container, and repeating the aforementioned steps.

The aforesaid process can be enhanced with the patient having greater freedom of movement if the dialysis solution container is in bag form, particularly a flexible, foldable plastic bag. In this manner, once the dialysis solution has exited the dialysis solution bag, the bag can be folded and carried about by the patient. A very effective connection and disconnection system between the dialysis solution bag and the patient's catheter tube can be achieved by using a luer lock connection system. In this manner, the transfer tube extending from the dialysis solution bag carries a first luer connector and the catheter tube extending from the patient's peritoneal cavity carries a complementary luer lock connector. The desirability of achieving, in the absence of liquid, and maintaining an uncontaminated connection at the luer connector is apparent and is achieved by means of the present invention.

It has been found desirable for the luer lock connector which is carried by the patient to be of a relatively permanent type, while the cooperating luer lock connector which is carried by the tubing extending from the solution container may be relatively disposable. Further, it is necessary that the luer lock connection be secure and that leakage be prevented in order to prevent contamination which could result in peritonitis.

Where the dialysis solution bag is such that it carries a transfer tube extending therefrom, which transfer tube couples to the patient's catheter tube, it may be desirable to prevent the dialysis solution within the dialysis solution bag from flowing into the transfer tube carried by the dialysis solution bag. By utilizing a frangible connector in series with the dialysis solution bag tubing, the flow of dialysis solution from the dialysis solution bag into the tubing can be prevented until the frangible connector is broken.

It is an object of the present invention to provide a novel solution container for continuous ambulatory peritoneal dialysis, which container is constructed so as to permit significant freedom of movement for the patient.

Another object of the present invention is to provide novel means for preventing the solution within the dialysis solution container from flowing into the transfer tubing of the dialysis solution container until a frangible member is broken, thereby allowing the connection to be made in the absence of liquid.

A further object of the present invention is to provide a novel luer lock connector which maintains the integrity of the connection and alleviates contamination.

Another object of the present invention is to provide a luer lock connection device which includes a multiple seal-type engagement between the male and female luer lock connectors thus preventing leakage and maintaining a water-tight bacteria barrier at the connection.

A still further object of the present invention is to provide a luer lock connection device in which one of the luer lock connectors is relatively permanent while the other luer lock connector may be relatively disposable.

Another object of the present invention is to provide a novel solution container for continuous ambulatory peritoneal dialysis having a particulate filter and clamping means in series with the transfer tube extending from the solution container so as to provide a simple but highly effective tubing set carried by the solution container, with the solution container being formed of a flexible, foldable plastic material.

Other objects and advantages of the present invention will become apparent as the description proceeds.

SUMMARY OF THE INVENTION

In accordance with the invention, equipment is provided for continuous ambulatory peritoneal dialysis in which a solution container is coupled via flexible tubing to a patient's tube that communicates with the patient's peritoneal cavity. The equipment comprises a flexible, foldable plastic dialysis solution container having a transfer port extending therefrom. A flexible tube extends from the transfer port and has a luer connection at its distal end for connecting to a luer connection carried by the patient's tube. The flexible tube may take many forms, such as a disposable tube carried by the dialysis solution container and extending continuously from the transfer port, or the flexible tube may be an intermediate, semi-permanent tubing set, both ends of which carry a luer connection; one connection is made with the patient's tube, the other with the luer connection which is connected to the transfer port of the solution container. This latter flexible tube (tubing set) is designed to be connected semi-permanently to the patient's tubing, being replaced approximately once per month. Alternatively, the flexible tube may comprise a number of separate, connected tubes, one or more of which carries a filter.

In the illustrative embodiments, a frangible member is provided in the transfer port or the flexible tube. The frangible member normally blocks fluid flow in the transfer port or the flexible tube but permits fluid flow after the frangible member is broken.

In an illustrative embodiment, a particulate filter is connected in series with the flexible tube. In addition, a manually-operable clamp is connected in series with the flexible tube.

In an illustrative embodiment, the flexible tube has a luer connector at its distal end for connecting to a luer connector carried by the patient's tube. The luer connector at the distal end and the patient's tube luer connector comprises a cooperating male luer lock connector and a female luer lock connector. The male luer connector has a central tubular portion defining an axial bore with at least a portion of the central tubular portion being enclosed by an outer sheath having a generally circular cross-sectional configuration. The outer sheath is internally threaded.

The female luer connector comprises a main tubular member which cooperatively engages the male luer central tubular portion to provide a first liquid seal. The main tubular member has an outwardly radially extending flange adjacent its distal end. In one embodiment, the flange takes the form of a single annular outwardly extending member. In another embodiment, the flange takes the form of external thread.

In one illustrative embodiment, an elastomeric member is carried by the female luer connector and is dimensioned and operable for providing a second liquid seal with the internal wall of the rigid outer sheath of the male connector to aid in maintaining a water-tight bacteria barrier at the luer lock connection. Further, the elastomeric member may be swabbed or the chamber defined by the outer sheath filled with a sterilizing agent by the patient, which would aid in preventing contamination of the system.

Alternatively, in another illustrative embodiment the female luer connector may have a rigid outer wall portion that is operable with the internal wall of an elastomeric outer sheath of the male connector for providing the second liquid seal.

In the other illustrative embodiment, the outer wall portion is contiguous with the external surface of the main tubular member and has a rearwardly extending outer taper. In this manner, the pressure engagement of the internal wall of the outer sheath and the outer wall portion will increase as the male and female connectors are threaded together.

In the other illustrative embodiment, the male and female luer lock connectors are each formed in an integral one-piece construction, and the female luer lock connector may be formed of stainless steel or titanium to provide a more permanent construction while the male luer lock connector is formed of a resilient plastic material which is readily disposable. It is, of course, apparent that a variety of materials may be used without departing from the scope of the present invention.

A more detailed explanation of the invention is provided in the following description and claims, and is illustrated in the accompanying drawings.

BRIEF DESCRIPTION OF THE DRAWINGS

FIG. 2 is a rear view of a male luer lock connector constructed in accordance with the principles of the present invention;

FIG. 3 is an elevational view of a male luer lock connector constructed in accordance with the principles of the present invention, with portions broken away for clarity;

FIG. 4 is a front view thereof;

FIG. 5 is a front view of a female luer lock connector constructed in accordance with the principles of the present invention;

FIG. 6 is an elevational view thereof, with portions broken away for clarity;

FIG. 7 is a greatly enlarged view of a portion of the female luer lock connector of FIG. 6;

FIG. 8 is an elevational view, with portions broken away for clarity, of a device for capping the female luer lock connector of FIG. 6;

FIG. 9 is an elevational view, with portions broken away for clarity, of a capping device for the male luer lock connector of FIG. 3;

FIG. 11 is an elevational view, with portions broken away for clarity, of another embodiment of a female luer lock connector constructed in accordance with the principles of the present invention;

FIG. 12 is an enlarged view of the cooperating portions of a male luer lock connector and the female luer lock connector of FIG. 11;

FIG. 14 is an elevational view, with portions broken away for clarity, of a device for capping the female luer lock connector of FIG. 11 or FIG. 15;

FIG. 15 is an elevational view, with portions broken away for clarity, of another embodiment of a female luer lock connector constructed in accordance with the principles of the present invention;

FIG. 16 is an elevational view, without portions broken away, of the female luer lock connector of FIG. 15;

FIG. 17 is an enlarged view of the cooperating portions of a male luer lock connector and the female luer lock connector of FIG. 15;

FIG. 18 is an elevational view, without portions broken away, of another embodiment of a female luer lock connector constructed in accordance with the principles of the present invention;

FIG. 19 is an elevational view, broken away for clarity, of the female luer lock connector of FIG. 18.

DETAILED DESCRIPTION OF THE ILLUSTRATIVE EMBODIMENT

Figure 1:
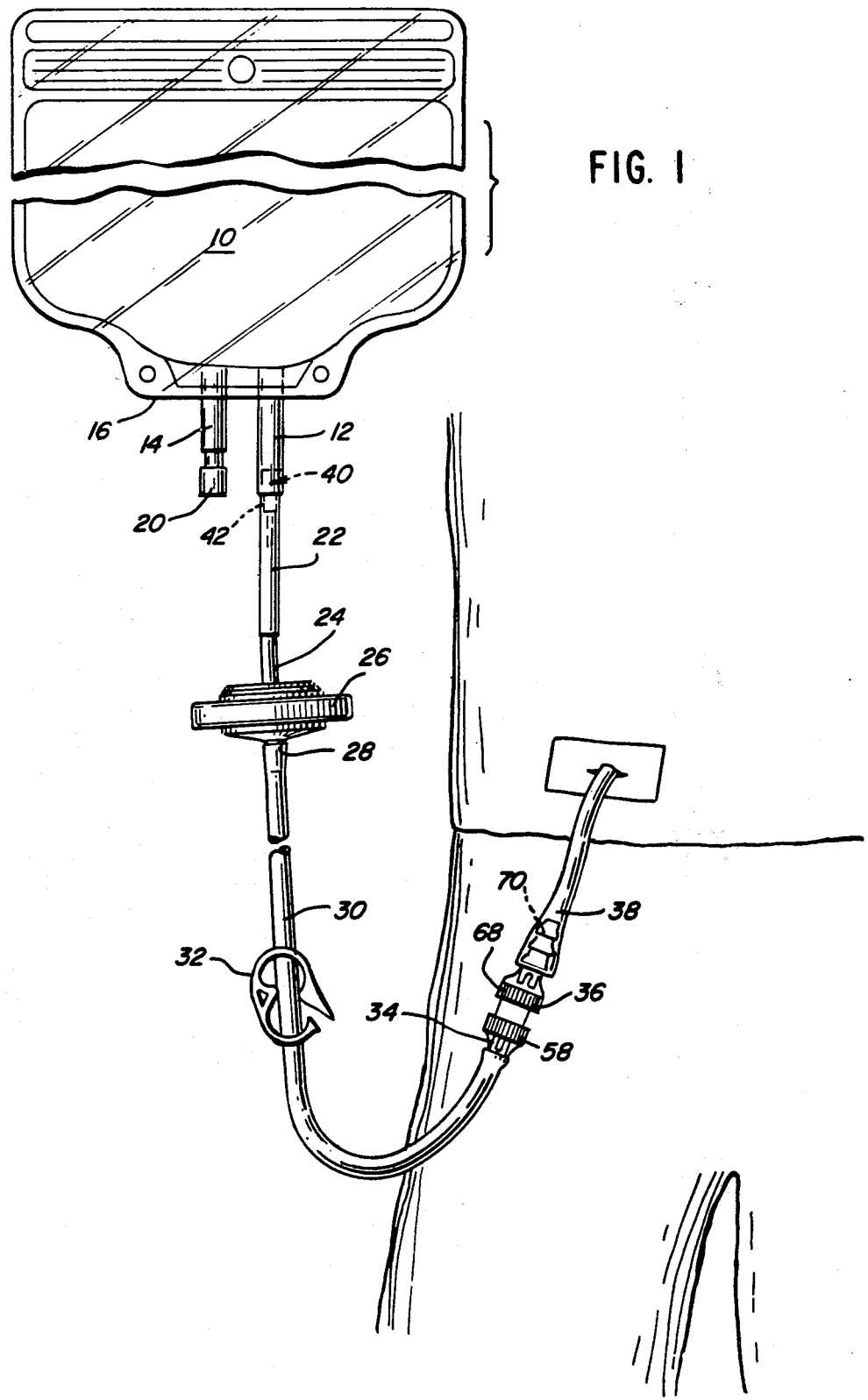
FIG. 1 is a view of a solution container for continuous ambulatory peritoneal dialysis, constructed in accordance with one embodiment of the present invention.

Referring to FIG. 1, a dialysis solution bag 10 is shown therein having ports 12 and 14 extending from one side 16 of the bag 10. Port 14 is capped with an injection site 20 in the illustrative embodiment.

Solution container 10 is preferably formed of flexible sheet plastic material that is heat sealed at its edges to form a solution bag. Flexible plastic tubing 22 extends from transfer port 12 and is coupled to the inlet 24 of a particulate filter 26, the outlet 28 of which is coupled to flexible tubing 30 carrying a manually operable clamp 32 in series therewith and having a male luer lock connector 34 at its distal end. Male luer lock connector 34 is connected to a female luer lock connector 36 which is carried at the distal end of a patient's catheter tube 38 which extends into the patient's peritoneal cavity. Additional details concerning the construction of the novel luer lock connection system formed by male luer lock connector 34 and female luer lock connector 36 are set forth below and are illustrated in FIGS. 2-9.

Figure 20:
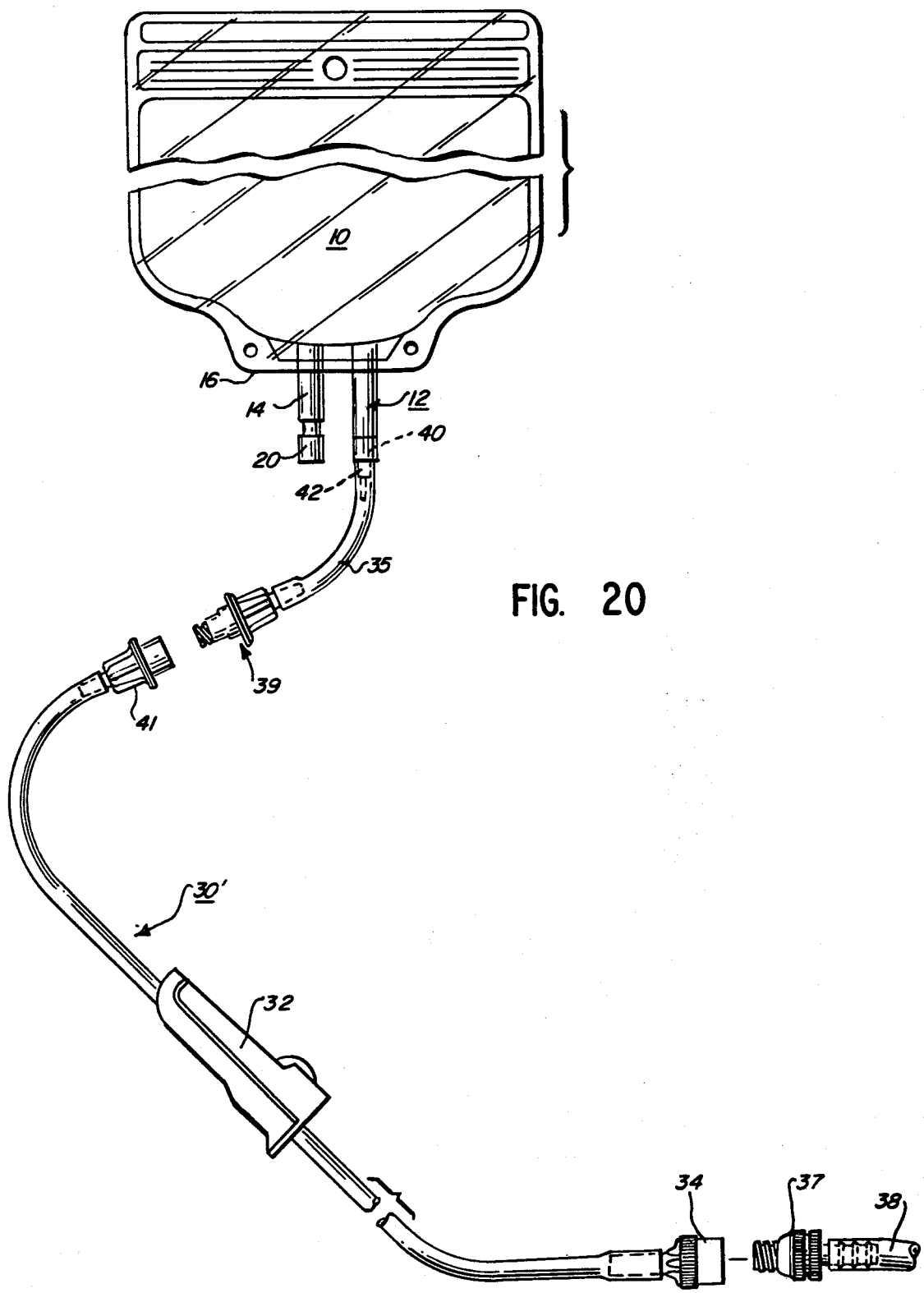
FIG. 20 is a view of a solution container for continuous ambulatory peritoneal dialysis, constructed in accordance with another embodiment of the present invention.

With tubing 30 attached directly to transfer port 12, the entire length of tubing 30 (and attached accessories) must be discarded at each container change. An alternative system has been used and is illustrated in FIG. 20. In this alternative system, the transfer port 12 includes an extended tube portion 35 having at its distal end a luer connector 39. Solution container 10 does not carry tubing 30. The length of tubing 35 from container 10 to the luer connector is relatively short, e.g., four inches.

As seen in FIG. 20, flexible tubing 30 is replaced by an intermediate semi-permanent tubing set 30' with luer connectors at each end. This intermediate set 30' can be of any desired length and carry any desired accessories, e.g., particulate filter, clamp and the like. One end of it carries a luer lock connector 41 for attachment to luer connector 39, the other end carries a luer lock connector 34 for attachment to the luer connector 37 connected to the patient's tubing 38. Although FIG. 20 shows tubing set 30' carrying male luer connectors 41 and 34 at its opposite ends for cooperative engagement with female luer connectors 39 and 37, respectively, if desired the male and female luer connectors could be switched, so that tubing set 30' would carry female luer connectors or a male luer connector and a female luer connector.

In the FIG. 20 embodiment, the length of flexible tubing 30' (the intermediate set) necessary to perform infusion and drain of peritoneal dialysis solution is carried by the patient rather than the solution container. In practice it has been found that this intermediate, semi-permanent set can be left attached to the luer connector 37 at the patient's tubing for several weeks without the need to change it. By reusing this intermediate set, and not having to discard tubing 30' at each container change, costs can be significantly reduced.

As seen in FIG. 1, a frangible member 40 is positioned in series with transfer port 12 and tubing 22, within the bore defined by the port and tubing. Frangible member 40 blocks fluid flow from transfer port 12 to tubing 22 until the frangible member 40 is broken. Frangible member 40 is preferably formed of a plastic material which fills the flow path of transfer port 12 and tubing 22, but defines a central bore through the plastic material which is sealed by a breakoff member 42. When member 42 is manually broken, the dialysis solution contained by solution bag 10 can flow past the frangible member 40 and thence through tubing 22 and downstream with respect thereto. In this manner, the dialysis solution within solution bag 10 is maintained adjacent transfer port 12 until frangible member 40 is broken, and not until the breaking of frangible member 40 can the solution contained within solution bag 10 flow downstream of the frangible member 40.

The filter 26 is a particulate type filter, having a pore size of approximately 5 microns and having a relatively large surface area. It is preferred that the surface area be at least 4 square centimeters and most desirably, about 7 square centimeters. It is also preferred that filter 26 comprise a hydrophilic membrane filter utilizing air venting by hydrophobic membranes.

Clamp 32 may be any type of flexible tubing clamp as is well-known in the art, with it preferably being a type of clamp which may be manually engaged and disengaged, using the thumb and forefinger.

Male luer connector 34 is illustrated in detail in FIGS. 2-4. Referring to these Figures, the male luer connector 34 comprises a central tubular portion 50 defining an axial bore 52, and with the central tubular portion 50 extending rearwardly to form a circular insert 50a. Insert 50a is solvent bonded within flexible tubing 30 and extends outwardly by means of a plurality of shoulders 54 to provide an outer sheath 56 which surrounds central tubular portion 50. Outer sheath 56 has a knurled manually-graspable portion 58 and carries first means 66 for cooperative locking with a female luer connector. First means 60 is illustrated in the form of internal threads 60. The outer sheath 56 aids in preventing touch contamination during locking and/or unlocking of the luer lock connection system and serves to carry the threads 60 which are engaged by second means 62 (FIG. 6) for cooperative locking with thread 60. Second means 62 comprises a flange 62 (FIG. 6) carried by female luer lock connector 36. In the FIG. 6 embodiment, flange 62 takes the form of a single annular outwardly extending member. In the embodiments of FIGS. 15-16 and 18-19, the flange takes the form of external threads 63.

Referring to FIGS. 5-7 in which the female luer lock connector 36 is shown in detail, it can be seen that connector 36 comprises a main tubular member 64 having outwardly radially extending flange 62 adjacent its distal end 66. A manually graspable ring 68 surrounds main tubular member 64 and is preferably formed integral therewith, with ring 68 also being formed integrally with a barbed rearward extension 70 for connection within the bore of the patient's catheter tube 38. A knurled portion 72 is provided on the external surface of ring 68 to aid in manually grasping the same. Rearward extension 70 is coupled to ring 68 by means of a plurality of shoulders 74, and the central tubular member 64 and rearwardly extending member 70 define a common axial bore 76.

The flange 62 is shaped and dimensioned so that when male luer lock connector 34 is engaged with female luer lock connector 36, central tubular portion 50 of connector 34 will enter bore 76, and flange 62 will be threaded along threads 60 to form a locking connection.

Figure 10:
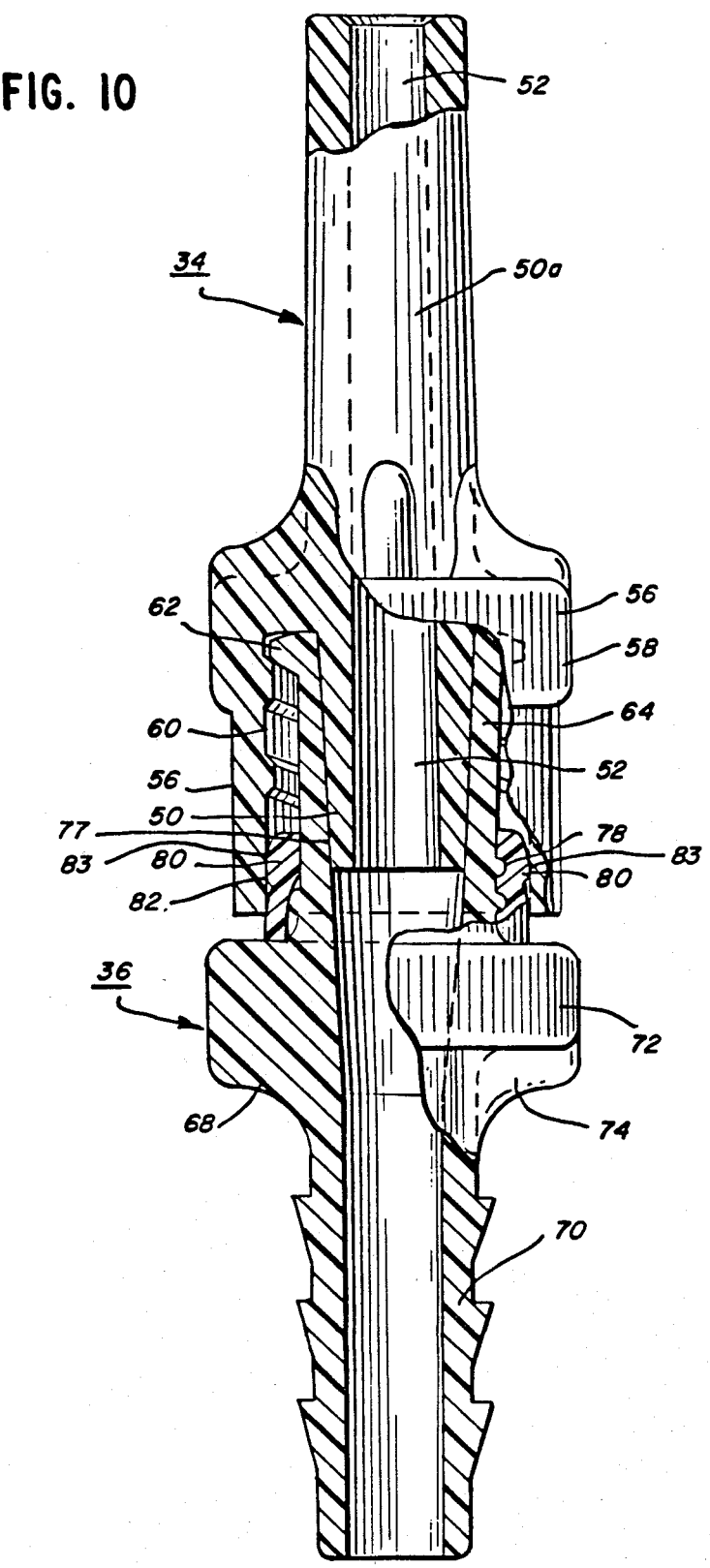
FIG. 10 is an elevational view of the male luer lock connector of FIG. 3 shown engaged with the female luer lock connector of FIG. 6, with portions broken away for clarity.

The diameter of bore 76 tapers inwardly from distal end 66, to a diameter that is smaller than the external diameter of central tubular portion 50, whereby a first liquid seal 77 (FIG. 10) will result between the external surface of central tubular portion 50 and the internal wall of bore 76 of tubular member 64. A liquid seal is a pressure engagement between two parts to aid in preventing flow of liquid past the pressure engagement.

Referring to FIGS. 6 and 7 in particular, it is seen that a number of projections or rings 78 are carried by tubular member 64 and an elastomeric member 80 surrounds the tubular member 64 and overlies the projections 78. Elastomeric member 80 has an outwardly extending annular bead 82 utilized for sealing purposes. Thus when male connector 34 and female connector 36 are engaged, elastomeric member 80 will enter outer sheath 56 and a second liquid seal 83 (FIG. 10) will be provided as a result of annular bead 82 engaging the internal wall of outer sheath 56 and being compressed thereby. In addition to providing an effective liquid seal 83 to prevent contamination, elastomeric member 80 also acts to provide a water-tight bacteria barrier which maintains the integrity of the locking connection thus preventing contamination of the luer connection.

If desired, elastomeric member 80 could be swabbed or the chamber defined by the outer sheath 56 could be filled by the patient with a sterilizing agent, such as Betadine solution. It is preferred that the female luer connector 36, with the exception of elastomeric member 80, be formed in a one-piece integral injection molding construction, and that elastomeric member 80 be formed in a subsequent step in the injection molding process during manufacture of the luer connector. Likewise, in this embodiment, it is preferred that the entire male luer connector 34 be formed in a one-piece unitary molded construction.

Under certain circumstances, the patient may desire to disconnect the luer lock connection once the dialysis solution has been introduced into the patient's peritoneal cavity. For this purpose, a cap 90 (FIG. 8) for capping the female luer connector is provided which includes a closed top portion 92 and a downwardly extending sidewall portion 94. Sidewall portion 94 defines a bore 96 which has an identical diameter to the opening defined by outer sheath 56, and the internal wall of sidewall portion 94 carries threads 98 which are identical in size and configuration to threads 60. A central tubular portion 50b is also provided. A knurled portion 100 is provided for enabling manual grasping of the cap 90.

Referring to FIG. 9, a cap 102 for capping the male luer connector is provided that is similar in configuration to female luer connector 36 except that it does not include rear tubular connector 70. Identical reference numerals have been used on the FIG. 9 cap to represent the portions of cap 102 which are identical to portions of female luer connector 36. It can be seen that instead of bore 76 extending continuously, the bore 76 is capped at its end 104. It should also be realized that male luer lock connector 34 may be carried by the patient's catheter tubing 38 with the female luer lock connector 36 being connected at the distal end of tube 30.

Referring to FIGS. 11 and 12, an alternative female luer lock connector 202 is illustrated with identical reference numerals indicating the portions of female luer lock connector 202 and male luer lock connector 210 which are identical to portions of female luer lock connector 36 and male luer lock connector 34, respectively.

It can be seen that connector 202 comprises a main tubular member 64 having outwardly radially extending flange 62 adjacent its distal end. Main tubular member 64 is contiguous with a manually-graspable ring 204 which extends contiguously rearwardly from the main tubular member 64, with ring 204 also being formed integrally with a barbed rearward extension 70 for connection with a flexible plastic tube, such as within the bore of the patient's catheter tube in continuous ambulatory peritoneal dialysis. A knurled portion 72 is provided on the rear external surface of ring 204 to aid in manually grasping the same. Rearward extension 70 is coupled to ring 204 and the main tubular member 64 and rearwardly extending member 70 to define a coaxial bore 76.

Figure 13:
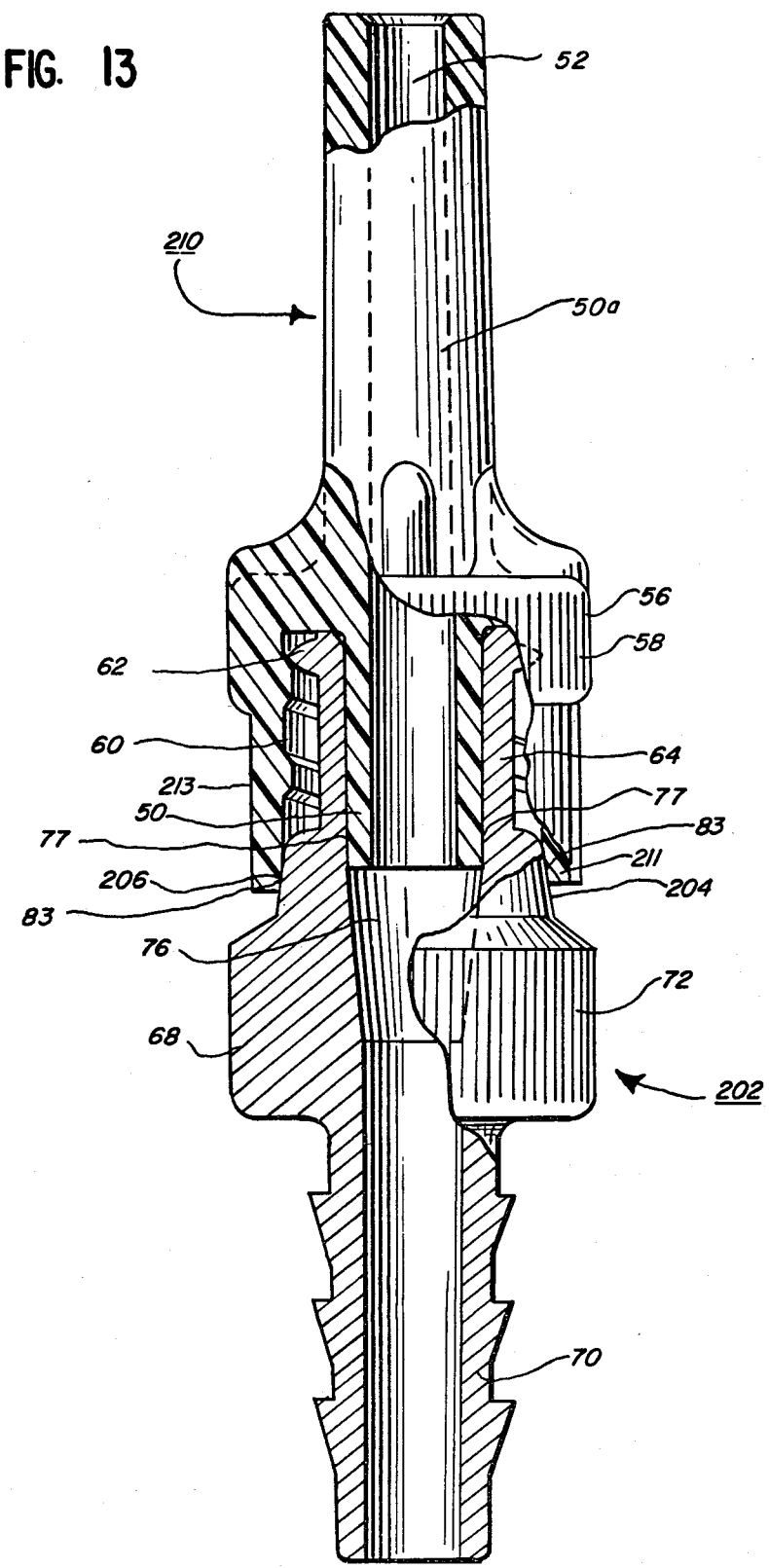
FIG. 13 is an elevational view of the male luer lock connector of FIG. 12 shown engaged with the female luer lock connector of FIG. 11, with portions broken away for clarity.

The male luer lock connector 210 shown in FIGS. 12 and 13 used with the female luer lock connector 202 shown in FIGS. 11 and 13 is identical to the male luer lock connector 34 shown in FIG. 3 with the exception that the front end 211 of the outer sheath 213 or the entire outer sheath 213 is formed of resilient material. This may be accomplished by separately molding the outer sheath 213 and then attaching it to a male luer connector or by providing a unitary member formed of the elastomeric resilient material desired.

Referring to FIG. 13, a first liquid seal 77 is formed at the engagement between the external surface of central tubular portion 50 and the internal wall of bore 76 of tubular member 64.

Outer wall portion 204 of female luer lock connector 202 has a rearwardly extending outward taper 206 so that the pressure engagement of the internal wall 212 of outer sheath 213 of the male luer connector 210 and outer wall portion 204 will increase as the male and female connectors are threaded together. The flange 62 is shaped and dimensioned so that when male luer lock connector 210 is engaged with female luer lock connector 202, central tubular portion 50 of connector 30 will enter bore 76 and flange 62 will be threaded along threads 60 to form a locking connection. The internal wall 212 of outer sheath 213 will engage tapered surface 206 of outer wall 204 snugly, and the engagement will become tighter as the luer connectors are threadedly closed tighter. In this manner, the cooperation of the internal wall of the outer sheath 213 and surface 206 of outer wall 204 is operable for providing the second liquid seal 83 to prevent leakage and to aid in maintaining a water-tight bacteria barrier.

If female luer lock connector 202 is coupled to a catheter tube which extends to the patient's peritoneal cavity, it is desirable that luer lock connector 202 be formed of a more permanent material. To this end, a stainless steel or titanium connector 202 would be satisfactory.

Referring to FIG. 14, the cap 91 shown therein is similar to the cap of FIG. 8 and the same reference numerals have been used for identical features. However, cap 91 has semicircular manually-graspable portion 97 which aids in threading the cap onto a female luer lock connector.

Referring to FIGS. 15 and 16, a female luer lock connector is shown therein and is similar in many respects to female luer lock connector 202 illustrated in FIG. 11. Identical reference numerals have been used in the illustrations of FIGS. 11, 15 and 16 to designate identical portions of these luer lock connectors.

The primary difference between the female luer lock connectors of FIG. 15 and FIG. 11 is that in the FIG. 11 embodiment, the flange 62 takes the form of a single annular outwardly extending member. In the FIGS. 15-16 embodiment, the flange takes the form of external threads 63. In addition, in the FIG. 11 embodiment there is a single knurled portion 72, while in the FIGS. 15-16 embodiment there are a pair of separated knurled portions 73 and 75.

Referring now to FIGS. 18 and 19, the female luer lock connector 39 shown therein is similar to female luer lock connector 202 of FIG. 11. One difference between the female luer lock connectors of FIGS. 18 and 11 is that in FIG. 11 the flange 62 takes the form of a single annular outwardly extending member while in the FIG. 18 embodiment the flange takes the form of external threads 63. Additional differences include the annular touch contamination protection ring 77 on the FIGS. 18-19 embodiment and visual indicator projections 79 and 81 on the FIGS. 18-19 embodiment, which assure that the male luer lock connector is securely connected to female luer lock connector 39. The female luer lock connector 39, and the visual indicator feature, are disclosed in a copending United States patent application in the name of T. Michael Dennehey, Ser. No. 101,246, filed Dec. 7, 1979 now U.S. Pat. No. 4,294,250.

The embodiment of the female luer lock connector of FIGS. 18-19 is preferably used (see FIG. 20) at the distal end of extended tube portion 35 of transfer port 12, in the method of practicing continuous ambulatory peritoneal dialysis wherein the patient carries a semi-permanent tubing set 30' connected to his catheter tubing 38.

It can be seen that the present invention provides a luer lock connection that is secure and prevents leakage in order to prevent contamination which could result in peritonitis. Thus in both embodiments, a first liquid seal is provided at the engagement of the external surface portion of the male luer with the internal surface portion of the female luer. Further, a second liquid seal is provided with the internal wall of the outer sheath when the male and female connectors are connected, to aid in maintaining a liquid-tight bacteria barrier at the luer lock connection. Thus a double sealed connection is provided when the male and female connectors are joined.

Although illustrative embodiments have been shown and described, it is to be understood that various modifications and substitutions may be made by those skilled in the art without departing from the novel spirit and scope of the present invention.

What is claimed is:

1. A luer lock connector attached to the end of flexible tubing, which comprises: a main tubular member proportioned to sealingly receive a mating luer lock connector within the bore of said main tubular member, said main tubular member being provided with flange-shaped protrusion means extending radially outwardly, said protrusion means being proportioned to cooperate with a matching thread of the mating luer lock connector for attachment thereto, the outer wall of said main tubular member being provided with an annular area spaced from the ends thereof and also spaced from the protrusion means, said annular area defining an enlarged diameter for annular engagement with an outer sheath of the mating connector to form a sealing area with said outer sheath sealingly surrounding and enclosing said annular area, said annular area being an integral part of said luer lock connector, said luer lock connector being made of titanium and being free of an attached sleeve surrounding said protrusion means and main tubular member.

2. The luer lock conenctor of claim 1 in which said flange-shaped protrusion means comprises a helical thread.

3. A luer lock connector for attachment to the end of flexible tubing, which comprises:
a main tubular member proportioned to sealingly receive a mating luer lock connector within the bore of said main tubular member, said main tubular member being provided with flange-shaped protrusion means extending radially outwardly, said protrusion means being proportioned to cooperate with a matching thread of the mating luer lock connector for attachment thereto, the outer wall of said main tubular member being provided with an annular area spaced from the ends thereof and also spaced from the protrusion means, said annular area being made of resiliently deformable material and defining an enlarged diameter for annular engagement with an outer sheath of the mating connector to form a sealing area with said outer sheath surrounding and enclosing said annular area, said luer lock connector being free of an attached sleeve surrounding said protrusion means and main tubular member.

4. A luer lock connector system which comprises a female luer lock connector in locked relation with a male luer lock connector, said female luer lock connector comprising a main tubular member sealingly receiving said male luer lock connector within the bore of said main tubular member, said main tubular member being provided with flange-shaped protrusion means extending radially outwardly, said protrusion means cooperating with a matching thread of the male luer lock connector for attachment thereto in locked relation; the outer wall of said main tubular member being provided with an annular area spaced from the ends thereof, and also spaced from the protrusion means, said annular area defining an enlarged diameter of resiliently deformable material for annular engagement with the male connector to form a sealing area, said female luer lock connector being free of an integrally attached sleeve surrounding said annular area and main tubular member, said male luer lock connector having a central tubular luer portion defining an axial bore projecting in sealing relation into the bore of the main tubular member, said male luer lock connector also defining an outer sheath which surrounds both said central tubular luer portion and the main tubular member, said outer sheath having a generally circular cross-sectional configuration and defining a free annular end, a portion of said outer sheath defining a threaded internal wall portion to serve as said matching thread in locking engagement with the flange-shaped protrusion means of said luer lock connector, said threaded internal wall portion being spaced from the free annular end of said sheath by a portion of the inner surface of said sheath which defines an annular sealing area free of threads, said annular sealing area surrounding said resiliently deformable annular area of enlarged diameter of the luer lock connector in annular sealing relation thereto.

5. The luer lock connector system of claim 4 in which said flange-shaped protrusion means of the luer lock connector comprises a helical thread.

6. The luer lock connector system of claim 4 in which the free annular end of the outer sheath is positioned beyond said central tubular luer portion to circumferentially enclose the entire length of said central tubular luer portion within said outer sheath.

7. The luer lock connector system of claim 4 which is attached to tubing communicating with the peritoneal cavity of a patient.

8. A luer lock connector system which comprises a female luer lock connector in locked relation with a male luer lock connector, said female luer lock connector comprising a main tubular member sealingly receiving said male luer lock connector within the bore of said main tubular member, said main tubular member being provided with flange shaped protrusion means extending radially outwardly, the outer wall of said female tubular member being provided with an annular area spaced from the ends thereof and also spaced from the protrusion means, said annular area defining an enlarged diameter for annular engagement with the male connector to form a sealing area, said female luer lock connector being free of an integrally attached sleeve surrounding said annular area and main tubular member; said male luer lock connector having a central tubular luer portion defining an axial bore projecting in sealing relation into the bore of the main tubular member, said male luer lock connector also defining an outer sheath which surrounds both said central tubular luer portion and the main tubular member and is positioned beyond said central tubular luer portion to circumferentially enclose the entire length of said central tubular luer portion within said outer sheath, said outer sheath having a generally circular cross-sectional configuration and defining a free annular end, a portion of said outer sheath defining a threaded internal wall portion in locking engagement with the flange-shaped protrusion means of the female luer lock connector, said threaded internal wall portion being spaced from the free annular end of said sheath by a portion of the inner surface of said sheath which defines an annular sealing area free of threads, said annular sealing area surrounding said flange-shaped protrusion means in annular sealing relation thereto, said outer sheath being made of a resiliently deformable material and said female luer lock connector being made of rigid material.

9. The luer lock connector system of claim 8 in which said flange-shaped protrusion means of the luer lock connector comprises a helical thread.

10. The luer lock connector system of claim 9 which is attached to tubing communicating with the peritoneal cavity of a patient.

11. The luer lock connector system of claim 8 in which said female luer lock connector is made of titanium.

12. A luer lock connector system which comprises a female luer lock connector in locked relation with a male luer lock connector, said female luer lock connector comprising a main tubular member sealingly receiving said male luer lock connector within the bore of said main tubular member, said main tubular member being provided with flange shaped protrusion means extending radially outwardly, the outer wall of said female tubular member being provided with an annular area spaced from the ends thereof and also spaced from the protrusion means, said annular area defining an enlarged diameter for annular engagement with the male connector to form a sealing area, said female luer lock connector being free of an integrally attached sleeve surrounding said annular area and main tubular member; said male luer lock connector having a central tubular luer portion defining an axial bore projecting in sealing relation into the bore of the main tubular member, said male luer lock connector also defining an outer sheath which surrounds both said central tubular luer portion and the main tubular member, said outer sheath having a generally circular cross-sectional configuration and defining a free annular end, a portion of said outer sheath defining a threaded internal wall portion in locking engagement with the flange-shaped protrusion means of the female luer lock connector, said threaded internal wall portion being spaced from the free annular end of said sheath by a portion of the inner surface of said sheath which defines an annular sealing area free of threads, said annular sealing area surrounding said flange-shaped protrusion means in annular sealing relation thereto, said outer sheath being made of a resiliently deformable material and said female luer lock connector being made of rigid material.

* * * * *